United States Patent [19]

Verbeek et al.

[11] 4,355,998

[45] Oct. 26, 1982

[54] REAGENT FOR THE QUANTITATIVE DETERMINATION OF WATER AND ITS USE THEREFOR

[75] Inventors: Antonie E. Verbeek, Bathmen; Jozef M. J. Mattheij, Deventer, both of Netherlands

[73] Assignee: J. T. Baker Chemicals B.V., Deventer, Netherlands

[21] Appl. No.: 292,880

[22] Filed: Aug. 14, 1981

[30] Foreign Application Priority Data

Sep. 2, 1980 [EP] European Pat. Off. ........ 80105224.2

[51] Int. Cl.$^3$ ............................................. G01N 33/18
[52] U.S. Cl. ............................. 23/230 R; 23/230 HC; 252/408
[58] Field of Search ............... 23/230 R, 230 HC; 252/408; 204/1 T

[56] References Cited

U.S. PATENT DOCUMENTS 3,656,907  4/1972  Delmonte ..................... 23/230 R

FOREIGN PATENT DOCUMENTS 2062859  5/1981  United Kingdom .

OTHER PUBLICATIONS

Verhoef et al., Analytica Chimica Acta, vol. 94, 1977, pp. 395-403.
Anon., Chemisch Weekblad Magazine, Mar. 1979, p. 135.

Primary Examiner—Arnold Turk
Attorney, Agent, or Firm—George W. Rauchfuss, Jr.

[57] ABSTRACT

A reagent for the quantitative determination of water, used together with an iodine-containing titrating solution, the reagent containing sulfur dioxide and an anhydrous alkali metal trimethyl acetate or a mixture of anhydrous alkali metal trimethyl acetate and an anhydrous alkali metal salicylate dissolved in 2-methoxy ethanol, methanol or in a mixture of 2-methoxy ethanol and methanol in a volume ratio of at least 10 to 90. This reagent is distinguished in that the increase of the blind value is minimized even at elevated temperatures.

17 Claims, No Drawings

REAGENT FOR THE QUANTITATIVE DETERMINATION OF WATER AND ITS USE THEREFOR

FIELD OF THE INVENTION

This invention relates to a reagent and method for quantitative determination of water in combination with a titration solution containing iodide.

BACKGROUND OF THE INVENTION

The usual method for quantitatively determining water is the Karl-Fischer method in which the substance to be analyzed is reacted with sulfur dioxide and iodine dissolved in a mixture of pyridine and methanol; see K. Fischer, Angew. Chemie, Vol. 48 (1935), page 394. The reagent reacts with water to give pyridine sulfate and hydrogen iodide. In this process the reagent undergoes decoloration. The iodine consumption is a measure for the water content of the substance. The reaction proceeds according to the following equation:

$$SO_2 + I_2 + 2H_2O \rightarrow H_2SO_4 + 2\ HI$$

The titrimetric determination is very accurate. The reagent allows a water content of less than 0.01% to be detected; see Kirk-Othmer, Encyclopedia of Chemical Technology, 2nd edition. Vol. 2 (1963), pages 673–677.

A disadvantage of the Karl-Fischer method is the fact that the reaction proceeds slowly, that titration is therefore laborious and time-consuming and that the endpoint is distorted. An inconvenience is the annoying odor caused by the sulfur dioxide and pyridine. Moreover pyridine makes it necessary to perform the process under a fume hood. Another disadvantage is the yellow $SO_2I^-$ complex formed by the sulfur dioxide and iodide which excludes the visual determination of the end point.

The limited shelf life, the instability of the titer and the necessity of storage in the dark and under cool conditions are further drawbacks.

The limited possibilities of use and the not very stable titration conditions are further problems which the analyst faces despite the fact that the Karl-Fischer method has been substantially improved.

In a known further development of this Karl-Fischer method the problems of the titrimetric determination of water are avoided; see J. C. Verhoef and E. Barendrecht, Analytica Chimica Acta, Vol. 94 (1977), pages 395–403. This improved method makes use of two reagents, namely a solution of sodium acetate and sulfur dioxide in methanol (solution A) and a solution of iodine in methanol (titration solution B).

The so-called blind value of solution A is a measure of its stability. In practice it has been found that the blind value of solution A increases at 18° to 20° C. during a week by 0.1 ml. The reason is that an ester reaction proceeds according to the scheme:

alcohol + acid → ester + water

This reaction becomes more noticeable at higher temperatures. In the present case the following esterification reaction takes place:

methanol + acetic acid → methyl acetate + water

Blind values of about 20 ml therefore appear especially in hot countries because of the ester reaction that takes place at the higher temperatures prevailing there.

SUMMARY OF THE INVENTION

The present invention is based on the surprising finding that the presence of 2-methoxyethanol, methanol or a mixture thereof and an alkali metal salt of the trimethyl acetic acid (pivalic acid, molecular weight 102.12; $(CH_3)_3CCOOH$) or a mixture of an alkali metal pivalate and an alkali metal salicylate significantly reduce the ester reaction in the solution A. Therefore, according to the invention an alkali metal salt of the trimethyl acetic acid (pivalic acid) is used instead of the alkali metal acetate employed in the above described known improved method. It was further found that the additional use of an alkali metal salt of the salicylic acid further curtails the ester reaction.

DETAILED DESCRIPTION OF THE INVENTION

In solution A for instance, the molarity of sodium pivalate (trimethyl acetic acid-sodium salt) is 1 and the molarity of sulfur dioxide is 0.4. According to APHA the color of the solution is 10 and the blind value is 0 to 4 ml of the titrating solution B per 20 ml of solution A.

The titrating solution B has a constant titer of 3.5 mg $H_2O$/ml. About 1 part of titrating solution B is needed per 2 parts of solution A.

The titration procedure is as follows: 20 ml of solution A are pretitrated with the titrating solution B under steady stirring and with moisture being excluded. A specified amount of the water-containing substance to be analyzed is then quickly placed into the titration vessel. The amount of the substance to be analyzed (amount of test sample) is to be adequately proportioned to the estimated amount of water present.

With the appropriate buffer capacity, it is possible to determine 70 to 80 mg of water in 20 ml of solution A. The titration vessel is closed, the buret adjusted and titration is started. During the whole titration procedure the solution is to be thoroughly mixed, such as for example, with a magnetic stirrer.

The bipotentiometric method is used in the most usual titrations for determining the end point. The reduction time is normally 20 seconds, at which time the point of equivalence is reached.

If a yellow coloring appears prior to the endpoint, then the buffer capacity was insufficient. The premature yellow coloring can be prevented by reducing the amount of the sample or increasing the amount of solution A.

With this method, aquametry without interference is possible in alcohols, alkanes, aromatic hydrocarbons, aldehydes, ketones, ethers, esters, salts with crystallization water, basic substances such as trishydroxymethylamino methane, lyophilized products, food, molecular sieves and granular fertilizers. This method also lends itself to the visual determination of the end-point.

The undesired time and temperature dependent increase of the blind value is avoided by the improved inventive composition of solution A.

Thus the problem underlying the invention is to develop an improved reagent for the quantitative determination of water. This reagent is based on the above-described known reagent solution A which is used together with the titrating solution B. When allowed to stand, the reagent forms minor precipitates only slowly even at elevated temperatures while at the same time the increase of the blind value is minimized.

This problem is solved thanks to the surprising finding that precipitates form only slowly and to a minor degree and the undesired high increase of the blind value is avoided if 2-methoxyethanol and/or methanol is/are used as solvent for the reagent solution A and an alkali metal salt of the trimethyl acetic acid is simultaneously added instead of an alkali metal acetate. Preferably, an alkali metal salicylate is also incorporated into the reagent solution A, with the result that the formation of a precipitate and the increase of the blind value are even more suppressed.

Thus the invention relates to a reagent for the quantitative determination of water used together with an iodine-containing titrating solution, the reagent containing sulfur dioxide and an anhydrous alkali metal salt of the trimethyl acetic acid in 2-methoxy ethanol, methanol or a mixture thereof as solvent, the volume ratio of a mixture of 2-methoxy ethanol and methanol being at least 10:90. According to a preferred embodiment, the reagent (reagent solution A) additionally contains an alkali metal salicylate. This reagent (solution A) is used together with the above-described titrating solution B in a generally known manner for the quantitative determination of water.

The solution A of the invention preferably contains the anhydrous lithium or sodium salts as alkali metal trimethyl acetate and optionally alkali metal salicylate. The sodium salts are preferred for economic reasons. The alkali metal trimethyl acetate and the alkali metal salicylate optionally used serve above all as buffer. The alkali metal trimethyl acetate is employed in a molar amount of 1.5 to 0.5, perferably 1.2 to 0.8 and optimally 1.1 to 0.9.

The alkali metal salicylate is used in a molar amount of 1.5 to 0.5, preferably 1.2 to 0.8, and optimally 1.1 to 0.9. The molar ratio of alkali metal trimethyl acetate to alkali metal salicylate is preferably 1:1. The solution A is preferably 1 molar, i.e. it can contain 0.5 mole of alkali metal trimethyl acetate and 0.5 mole of alkali metal salicylate.

The sulfur dioxide is used in a molar amount of 0.7 to 0.1, preferably 0.5 to 0.2, optimally 0.45 to 0.35.

The iodine is used in the titrating solution B in a molar amount of 0.3 to 0.1, preferably 0.25 to 0.15, and optimally 0.23 to 0.19.

Of course, the reagent solutions contain the ingredients in amounts proportioned to each other. The solvent used for the solution A and the titrating solution B, that is the 2-methoxy ethanol, the methanol or the mixture of 2-methoxy ethanol and methanol should preferably be anhydrous. By anhydrous is understood here products with a water content of at most 0.05 percent by weight. Such products are commercially available.

If a mixture of 2-methoxy ethanol and methanol is used for the solution A, then the volume ratio is at least 10:90, preferably 15:85 to 25:75.

In practice the reagents for the determination of water are prepared in the following manner:
(a) First, nitrogen is introduced under stirring into anhydrous 2-methoxy ethanol or into a mixture of anhydrous 2-methoxy ethanol and anhydrous methanol during 15 to 30 minutes. In this way, small amounts of air or oxygen are separated from the solvent.
(b) The desired amount of anhydrous alkali metal pivalate or of a mixture of anhydrous alkali metal pivalate and alkali metal salicylate (dried or lyophilized for 15 to 30 hours at 110° to 120° C.) is then added in small portions under stirring and is dissolved. At the same time nitrogen is blown into the solution.
(c) After the alkali metal pivalate or the mixture of alkali metal pivalate and alkali metal salicylate have completely dissolved, nitrogen is introduced under stirring into the solution for another 15 to 30 minutes.
(d) Finally, the desired amount of sulfur dioxide is slowly introduced into the solution yielding the solution A.

The titrating solution B is prepared in the following manner:

Under stirring, the desired amount of iodine is introduced into anhydrous 2-methoxy ethanol, anhydrous methanol or a mixture of anhydrous 2-methoxy ethanol and anhydrous methanol and dissolved therein.

The reagents of the invention keep well at room temperature in tightly sealed bottles.

The following examples are illustrative of the invention.

EXAMPLE 1

Nitrogen is blown into 158 kg of anhydrous methanol for 15 minutes under stirring. 12.4 kg of dried sodium trimethyl acetate and 16 kg of alkali metal salicylate are then added in small portions under stirring and dissolved. The solution obtained once the substances have completely dissolved is stirred while nitrogen is blown into it for another 15 minutes. 5.1 kg of sulfur dioxide are then slowly added within 4 hours, yielding solution A which can be used for the quantitative determination of water together with a titrating solution of iodine in methanol, 2-methoxy ethanol or in a mixture of 2-methoxy ethanol and methanol.

The titrating solution B is prepared in the following manner:

5.4 kg of iodine are dissolved in 79 kg of anhydrous methanol or 96 kg of anhydrous 2-methoxy ethanol.

EXAMPLE 2

Solution A is prepared according to Example 1, however a mixture of 120.1 kg of anhydrous methanol and 36.5 kg of anhydrous 2-methoxy ethanol is used as well as 24.8 kg of dried sodium trimethyl acetate and 5.1 kg of sulfur dioxide.

EXAMPLES 3A and 3B

Example 2 is repeated, however a mixture of methanol and 2-methoxy ethanol is used in the volume ratio of 75:25 and 90:10.

EXAMPLES 4A and 4B

Examples 1 and 2 are repeated, however 20.4 kg of lithium trimethyl acetate are used instead of 24.8 kg of sodium trimethyl acetate and 10.2 kg of lithium trimethyl acetate instead of 12.4 kg of sodium trimethyl acetate, respectively.

These solutions, too, can be successfully used in the manner described above for the quantitative determination of water.

EXAMPLE 5

Examples 1 is repeated, however 6.4 kg and not 5.1 kg of sulfur dioxide are used.

EXAMPLE 6

Example 1 is repeated, however 3.2 kg and not 5.1 kg of sulfur dioxide are used.

COMPARATIVE TEST 1

Nitrogen is blown for 15 minutes under stirring into a mixture of 120.1 kg of anhydrous methanol and 36.5 kg of anhydrous 2-methoxy ethanol. 15.6 kg of anhydrous sodium acetate which was dried for 24 hours at 150° C. is then added in small portions under stirring and dissolved. The mixture obtained after the substances have completely dissolved is stirred while nitrogen is blown into it for another 15 minutes. 6.1 kg of sulfur dioxide are then slowly introduced within 4 hours. The resultant solution A can be used for the quantitative determination of water together with the titrating solution of iodine in methanol, 2-methoxy ethanol or in a mixture of 2-methoxy ethanol and methanol.

The titrating solution B is prepared in the following manner:

5.4 kg of iodine are dissolved in 79 kg of anhydrous methanol or 96 kg of anhydrous 2-methoxy ethanol.

COMPARATIVE TEST 2

Comparative Test 1 is repeated, however 3.33 kg and not 6.1 kg of sulfur dioxide are used.

The table below shows the stability of the blind value (consumption of titrating solution B per 20 ml of solution A) of the solutions A prepared according to Examples 1, 5 and 6 and comparative tests 1 and 2.

TABLE

|  | Ex. 1 | Ex. 2 | Ex. 5 | Ex. 6 | Comp. Test 1 | Comp. Test 2 |
|---|---|---|---|---|---|---|
| Start (20° C.) | 1.5 ml | 1.60 ml | 1.4 ml | 1.3 ml | 0.9 ml | 1.2 ml |
| After 2 weeks | 1.5 ml | 1.60 ml | 1.5 ml | 1.3 ml | 1.8 ml | 1.4 ml |
| After 3 weeks | 1.55 ml | 1.65 ml | 1.6 ml | 1.3 ml | 2.2 ml | 1.6 ml |
| After 4 weeks | 1.60 ml | 1.70 ml | 1.6 ml | 1.3 ml |  |  |
| At 40° C. |  |  |  |  |  |  |
| After 2 weeks | 1.5 ml | 1.6 ml | 1.5 ml | 1.3 ml | 4.3 ml | 2.2 ml |
| After 3 weeks | 1.6 ml | 1.7 ml | 1.65 ml | 1.3 ml | 6.1 ml | 2.7 ml |
| After 4 weeks | 1.7 ml | 1.8 ml | 1.80 ml | 1.4 ml |  |  |
| At 5° C. |  |  |  |  |  |  |
| After 2 weeks | 1.50 ml | 1.6 ml | 1.40 ml | 1.30 ml | 0.9 ml | 1.2 ml |
| After 3 weeks | 1.50 ml | 1.6 ml | 1.40 ml | 1.30 ml | 0.9 ml | 1.2 ml |
| After 4 weeks | 1.50 ml | 1.6 ml | 1.40 ml | 1.30 ml |  |  |

As is evident from the table, the blind value remains stable thanks to the inventive composition of the reagent of Examples 1, 2, 5 and 6 and consequently the problem posed of developing a stable solution A for each working temperature is successfully solved. The table also shows that the blind value is even more stable if the solution contains less sulfur dioxide (Example 6).

Finally it can be seen from the table that the blind value is less stable especially at higher temperatures, if the solutions A do not contain the invention addition of alkali metal trimethyl acetate and optionally of alkali metal salicylate (Comparative Tests 1 and 2).

Test A

The reagent solution of Example 1 and the titrating solution B is used for determining water in petroleum ether having a boiling point of 100° to 140° C. The test is carried out in the following manner:

20 ml of the solution A are pretitrated with the titrating solution B while the contents of the reaction vessel are stirred and agitated and moisture is excluded. 25 ml of petroleum ether are then quickly placed into the titration vessel. After the titration vessel is closed and the buret is adjusted, titration is commenced. 0.18 ml of the titrating solution B are used up. This corresponds to a 0.004 percent water content of the petroleum ether.

Test B

Test A is repeated with the reagent solution of Example 4. The petroleum ether has a water content of 0.004 percent.

In a further test the reagent solution of Example 4 is used for the determination of water of technical acetone. 5 ml of acetone are placed into the titration vessel and take up 2.28 ml of titrating solution B. This corresponds to a 0.26 percent water content of the acetone.

Test C

Test A is repeated with the reagent solution of Example 1 and Example 5. The following results are obtained:

Water content of the petroleum ether (when the reagent solution of Example 1 is used)=0.004 percent Water content of the petroleum ether (when the reagent solution of Example 5 is used)=0.004 percent The water content of edible oil is determined in a further test using the reagent solution of Example 5. The test is carried out in the following manner:

20 ml of the solution A are pretitrated with the titrating solution B while the contents of the reaction vessel are stirred and agitated and moisture is excluded. 10 ml of edible oil are then quickly placed into the titration vessel. After the titration vessel is closed and the buret is adjusted, titration is commenced. 1.13 ml of the titration solution B are used up. This corresponds to a 0.05 percent water content of the edible oil.

We claim:

1. In a reagent for the quantitative determination of water, used together with an iodine-containing titrating solution, the reagent containing sulfur dioxide and anhydrous alkali metal carboxylic acid salt in an anhydrous lower monohydric aliphatic alcohol as solvent, the improvement wherein the lower monohydric aliphatic alcohol is 2-methoxy ethanol, methanol or a mixture of both compounds in a volume ratio of at least 10:90 and that the anhydrous alkali metal carboxylic acid salt is an alkali metal trimethyl acetate.

2. In a reagent for the quantitative determination of water used together with an iodine-containing titrating solution, the reagent containing sulfur dioxide and anhydrous alkali metal carboxylic acid salt in an anhydrous lower monohydric aliphatic alcohol as solvent, the improvement wherein the lower monohydric aliphatic alcohol is 2-methoxy ethanol, methanol or a mixture of both compounds in a volume ratio of at least 10:90 and that the anhydrous alkali metal carboxylic acid salt is an alkali metal trimethyl acetate in admixture with an alkali metal salicylate.

3. The reagent according to claim 1, characterized in that the alkali metal trimethyl acetate is anhydrous lithium trimethyl acetate.

4. The reagent according to claim 2, characterized in that the alkali metal trimethyl acetate is anhydrous lithium trimethyl acetate.

5. The reagent according to claim 1, characterized in that the alkali metal trimethyl acetate is anhydrous sodium trimethyl acetate.

6. The reagent according to claim 2, characterized in that the alkali metal trimethyl acetate is anhydrous sodium trimethyl acetate.

7. The reagent according to claim 2 characterized in that the alkali metal salicylate is anhydrous sodium salicylate.

8. The reagent according to claim 4 characterized in that the alkali metal salicylate is anhydrous sodium salicylate.

9. The reagent according to claim 6 characterized in that the alkali metal salicylate is anhydrous sodium salicylate.

10. The reagent according to claim 1 characterized in that the volume ratio of the mixture of 2-methoxy ethanol and methanol is from 15:85 to 25:75.

11. The reagent according to claim 2 characterized in that the volume ratio of the mixture of 2-methoxy ethanol and methanol is from 15:85 to 25:75.

12. The reagent according to claim 1 characterized in that the sulfur dioxide concentration is 0.5 to 0.2 mole.

13. The reagent according to claim 2 characterized in that the sulfur dioxide concentration is 0.5 to 0.2 mole.

14. The reagent according to claim 1, characterized in that the alkali metal trimethyl acetate is present in a molar amount of 1.5 to 0.5.

15. The reagent according to claim 2, characterized in that the alkali metal trimethyl acetate and the alkali metal salicylate are present in a molar ratio of 1:1.

16. The use of the reagent of claim 1 for the quantitative determination of water together with an iodine-containing titrating solution.

17. The use of the reagent of claim 2 for the quantitative determination of water together with an iodine-containing titrating solution.

* * * * *